US00PP28971P3

(12) United States Plant Patent
Vijverberg

(10) Patent No.: US PP28,971 P3
(45) Date of Patent: Feb. 20, 2018

(54) ***MANDEVILLA* PLANT NAMED 'OOSMANPIN2'**

(50) Latin Name: ***Mandevilla sanderi* (Hemsl.) Woodson**
Varietal Denomination: OOSMANPIN2

(71) Applicant: Houdstermaatschappij Oosterom B.V., Waddinxveen (NL)

(72) Inventor: Petrus Cornelis Vijverberg, Naaldwijk (NL)

(73) Assignee: Houdstermaatschappij Oosterom B.V., Waddinxveen (NL)

( * ) Notice: Subject to any disclaimer, the term of this patent is extended or adjusted under 35 U.S.C. 154(b) by 0 days.

(21) Appl. No.: 15/330,647

(22) Filed: Oct. 24, 2016

(65) Prior Publication Data

US 2017/0118893 P1 Apr. 27, 2017

(30) Foreign Application Priority Data

Oct. 26, 2015 (QZ) ..... PBR 2015/2460

(51) Int. Cl.
*A01H 5/02* (2006.01)

(52) U.S. Cl.
USPC ..... Plt./232

(58) Field of Classification Search
USPC ..... Plt./232
See application file for complete search history.

*Primary Examiner* — Susan McCormick Ewoldt
(74) *Attorney, Agent, or Firm* — Samuel R. McCoy, Jr.

(57) ABSTRACT

A new and distinct *Mandevilla* cultivar named 'OOSMANPIN2' which is characterized by a compact growth habit, dark green and glossy foliage, large bright pink flowers, a prolific and continuous bloom habit, as well as the stability of these characteristics from generation to generation.

1 Drawing Sheet

Latin name of the genus and species: The Latin name of the genus and species of the novel variety disclosed herein is *Mandevilla sanderi* (Hemsl.) Woodson.

Variety denomination: The inventive variety of *Mandevilla* disclosed herein has been given the variety denomination 'OOSMANPIN2'.

CROSS REFERENCE TO RELATED APPLICATIONS

This application claims priority to the Community Plant Variety Rights application number 2015/2460, filed Oct. 26, 2015, which is herein incorporated by reference.

BACKGROUND OF THE INVENTION

Parentage: Over the course of many years, the inventor sourced various *Mandeville sanderi* (all non-patented) plants with flower colors ranging from white to pink to red. From this plant material, the inventor made selections of individual plants as well as single branches of individual plants, based on flower color, earliness of flowering, compactness of the plant, persistence of flowering, persistence in keeping flower color during the flowering. Many individual varieties were identified, and some were isolated for further evaluation. The candidate variety is the result of this selection process, and was first observed in the spring of 2014 in Westland, The Netherlands.

Asexual Reproduction: Asexual reproduction of the new cultivar 'OOSMANPIN2', by way of softwood stem cuttings, was first initiated in the summer of 2014 in Westland, The Netherlands. Through more than 10 subsequent generations, the unique features of this cultivar have proven to be stable and true to type.

SUMMARY OF THE INVENTION

The cultivar 'OOSMANPIN2' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OOSMANPIN2'. These characteristics in combination distinguish 'OOSMANPIN2' as a new and distinct *Mandevilla* cultivar:

1. *Mandevilla* 'OOSMANPIN2' exhibits a compact growth habit; and
2. *Mandevilla* 'OOSMANPIN2' exhibits dark green and glossy foliage; and
3. *Mandevilla* 'OOSMANPIN2' exhibits large bright pink, glossy flowers; and
4. *Mandevilla* 'OOSMANPIN2' exhibits prolific, continuous flowering.

BRIEF DESCRIPTION OF THE FIGURES

The figure illustrates, as nearly true as it is reasonably possible to make the same in color photographs of this type, an exemplary plant of 'OOSMANPIN2' in flower, grown in a commercial greenhouse in Honselersdijk, the Netherlands.

BOTANICAL DESCRIPTION OF THE PLANT

The following observations and measurements were made in January of 2017 and describe averages from a sample set of six specimens of 3 month old 'OOSMANPIN2' plants grown in 9 cm nursery pots grown in a greenhouse in Westland, The Netherlands. Plants were watered with overhead irrigation and fertilizer was applied using fertigation. No pest or disease measures were taken.

Those skilled in the art will appreciate that certain characteristics will vary with older or, conversely, with younger plants. 'OOSMANPIN2' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'OOSMANPIN2' and comparisons with other varieties of *Mandevilla* are provided below.

Plant description:

*Growth habit*.—Compact vining perennial; broad upright.

*Plant shape*.—Obovate to broad obovate.

*Average height from base to top of foliage*.—20.6 cm.

*Average height from base to top of the floral plane*.—20.4 cm.

*Average width*.—20.0 cm.

*Growth rate*.—Low to moderate.

*Plant vigor*.—Low to moderate.

*Propagation method*.—Softwood stem cuttings; rooting is in initiated in approximately 10 to 14 days under greenhouse conditions.

*Time to produce a finished plant*.—Approximately 6 to 9 months, depending on pot size, is required to produce a fully rooted and marketable plant when grown in a greenhouse with a minimum ambient temperature of 14 degrees Celsius.

*Disease and pest resistance or susceptibility*.—Plants have not been observed to be susceptible or resistant to pathogens and pests common to *Mandevilla sanderi*.

*Environmental tolerances*.—Adapt to at least USDA Zones 10 and 12, and temperatures ranging from at least 5 degrees to 40 degrees Celsius; moderate tolerance to rain; low to moderate tolerance to wind; low tolerance to drought.

Root system:

*General*.—Freely branching; moderately dense rooting.

*Texture*.—Fibrous.

*Color*.—Light brown.

Stem:

*Branching habit*.—Basally branching main stem; freely branching with lateral branches.

*Number of main stems per plant*.—Two.

*Number of lateral branches per plant*.—Four.

*Appearance; cross-section*.—Rounded.

*Length of lateral branches*.—13.3 cm.

*Diameter of lateral branches*.—0.3 cm at the widest point.

*Internode length on lateral branches*.—2.1 cm.

*Aspect*.—Upright; angle is approximately 75 to 80 degrees from horizontal plane.

*Strength*.—Strong.

*Color, juvenile*.—Yellow-green, nearest to RHS 144A.

*Color, mature*.—Yellow-green, in between RHS 144A and 144B.

*Color at internodes*.—Yellow-green, in between RHS 144A and 144B.

*Texture and luster*.—Glabrescent and moderately glossy.

*Color of bark on main stems*.—Greyed-brown, in between RHS N199C and N199D.

*Other stem characteristics*.—Stems produce a milky sap when damaged.

Foliage:

*Arrangement*.—Opposite.

*Quantity*.—Approximately 14 leaves per stem, as observed.

*Division*.—Simple.

*Lamina*.—Dimensions — 5.0 cm long and 3.5 cm wide, on average. Shape — Oblong to slightly obovate or ovate. Aspect — Nearly flat; slightly reflexed. Apex — Short apiculate. Base — Truncate. Margin — Entire; not undulated. Pubescence, texture and luster of adaxial surface — Glabrous, smooth, and moderately glossy. Pubescence, texture and luster of abaxial surface — Glabrous, smooth, and moderately glossy. Dimensions — 5.1 cm long and 3.8 cm wide, on average. Color — Juvenile foliage, adaxial surface — In between green, nearest to RHS 139A, and yellow-green, nearest to RHS 147A. Juvenile foliage, abaxial surface — Yellow-green, nearest to RHS 146A, and suffused with greyed-brown at the margins, nearest to RHS N199A. Mature foliage, adaxial surface — In between green, nearest to RHS NN137A, and yellow-green, nearest to RHS 147A. Mature foliage, abaxial surface — Yellow-green, nearest to RHS 146B, and heavily suffused with greyed-brown, nearest to RHS 199A. Venation — Pattern — Pinnate. Venation color, adaxial surface — Yellow-green, in between RHS 148A and 148B. Venation color, abaxial surface — Yellow-green, nearest to RHS 145A.

*Petiole*.—Length — 0.6 cm. Width — 0.2 cm. Texture — Smooth and glabrous. Luster — Moderately glossy. Strength — Moderately strong. Color, adaxial surface — Yellow-green, nearest to RHS 152A. Color, abaxial surface — Yellow-green, nearest to RHS 147C.

Inflorescence:

*Inflorescence arrangement*.—Terminal and axillary cymes bearing 2 to 6 flowers.

*Natural flowering season*.—Spring through autumn in USDA Hardiness Zones 10 through 12.

*Time to flower*.—Approximately 10 weeks from planting a rooted cutting.

*Dimensions*.—8.4 cm high and 8.5 cm in diameter.

*Quantity of flowers per inflorescence*.—4 on average; varying from 2 to 6.

*Quantity of flowers per plant*.—2.

*Quantity of flower buds per plant*.—17.

*Quantity of flowers and flower buds per plant*.—19.

*Peduncle*.—Dimensions — 0.8 cm long and 0.2 cm in diameter. Aspect — Upward and outward; at approximately 60 degrees to the lateral branch axis. Strength — Medium. Texture and luster — Glabrous and moderately glossy. Color — Yellow-green, nearest to RHS 146D.

Bud:

*Shape*.—Oblong, elongated; long pointed ovoid at the distal end.

*Dimensions.*—5.3 cm long and 1.2 cm in diameter.

*Pubescence, texture and luster.*—Glabrous, smooth and very slightly glossy.

*Color.*—The distal one-third portion of the bud is red, in between RHS N45A and 46A; the middle one-third section is yellow-green, in between RHS 145B and 145C; the proximal portion of the bud is yellow-green, in between RHS 144B and 144C.

Flower:

*Flowering habit.*—Moderately free to freely flowering.

*Shape.*—Funnelform.

*Vertical height.*—6.2 cm.

*Diameter.*—6.4 cm.

*Diameter of floral tube.*—1.7 cm, at its widest point.

*Length of floral tube.*—4.2 cm.

*Aspect.*—Flowers are outward facing.

*Fragrance.*—A faint pleasant fragrance; acidic-sweet.

*Lastingness.*—Approximately 10 days.

*Persistent.*—Self-cleaning.

*Pedicels.*—Dimensions — 0.5 cm long and 0.15 cm in diameter. Aspect — Upward and outward; approximately 20 degrees to the peduncle axis. Strength — Medium. Texture and luster — Glabrous, smooth, and moderately glossy. Color — Yellow-green, nearest to RHS 146D.

*Petals.*—Quantity of Petals — 5. Arrangement — Single whorl; petals imbricate and fused into an elongated tube at the base; lower 52.5 percent of the petals are fused. Shape of petal lobes — Spatulate. Dimensions, free portion of petals — 8.0 cm long and 2.8 cm wise. Apex — Bluntly apiculate. Base — Truncate; fused at the base. Margin — Entire; moderately undulated. Aspect — Moderately reflexed. Pubescence, texture and luster of upper surface — Glabrous, moderately velvety and matte. Pubescence, texture and luster of lower surface — Glabrous, slightly velvety and slightly glossy. Petal lobe color when opening, upper surface — Red, in between RHS 50A and 50B. Petal lobe color when opening, lower surface — Red, nearest to a combination of RHS 53C, 54B and 54D; occasionally striped with a lighter shade of red, nearest to RHS 56D. Petal lobe color when fully opened, upper surface — Red, in between RHS 52A and 52B. Petal lobe color when fully opened, lower surface — Red, nearest to a combination of RHS 53C, 54B and 54D; occasionally striped with a lighter shade of red, nearest to RHS 56D. Inner corolla tube color, when fully opened — Yellow, nearest to RHS 12A, with yellow veining, nearest to RHS 12A. Outer corolla tube color, when fully opened — Yellow-green, RHS N144B, with yellow-green veining, nearest to RHS N144B.

*Sepals.*—Calyx dimensions — 0.45 cm in diameter and 0.6 cm tall. Arrangement — Sepals are free, rotate. Quantity — 5. Shape — Narrow triangular. Sepal dimensions — 0.5 cm long and 0.2 cm wide at the base. Apex — Narrow acuminate. Base — Cuneate. Margin — Entire; not undulated. Pubescence, texture and luster, upper surface — Smooth; glabrous; matte. Pubescence, texture and luster, lower surface — Smooth; glabrous; matte. Color when opening, upper surface — Yellow-green, nearest to RHS 146D; upper half is suffused with red, in between RHS 53C and 53D. Color when opening, lower surface — Yellow-green, nearest to RHS 146D; upper half is suffused with red, in between RHS 53B and 53C. Color when fully opened, upper surface — Yellow-green, nearest to RHS 146D; upper half is suffused with red, in between RHS 53C and 53D. Color when fully opened, lower surface — Yellow-green, nearest to RHS 146D; upper half is suffused with red, in between RHS 53B and 53C.

Reproductive organs:

*Androecium.*—Stamen quantity — 5. Attachment — Adnate. Filament length — 0.2 cm. Filament color — Yellow-green, nearest to RHS 153D. Anther attachment — Basifixed. Anther shape — Oblong; with longitudinal dehiscence. Anther length — 0.9 cm. Anther width — 0.175 cm. Anther color — Greyed-yellow, nearest to RHS 162D. Anther aspect — The five anthers are touching at their apices, thus forming a cone of anthers. Pollen, presence — None detected.

*Gynoecium.*—Pistil quantity — One. Pistil length — 2.1 cm. Style length — 1.9 cm. Style color — Yellow-green, nearest to RHS 145D. Stigma shape — Club-shaped. Stigma length — 0.2 cm. Stigma diameter — 0.175 cm. Stigma color — Yellow-green, nearest to RHS 151B, and fading to white at the apex, nearest to RHS 155A. Ovary color — Yellow-green, nearest to RHS 144A.

Seed and fruit: None observed.

COMPARISONS WITH THE PARENT PLANTS

Plants of the new cultivar 'OOSMANPIN2' differ from the unnamed *Mandevilla sanderi* (Hemsl.) Woodson parent by the characteristics described in Table 1.

TABLE 1

| Characteristic | 'OOSMANPIN2' | Unnamed seed parent |
|---|---|---|
| Time to flower. | Flowers 2 to 3 weeks earlier than the species. | Flowers 2 to 3 weeks later than 'OOSMANPIN2'. |
| Growth habit. | More compact than the species. | Less compact than 'OOSMANPIN2'. |
| Flower color, when opening. | More bright pink. | Less bright pink. |
| Flower color fading. | Not fading. | Fades to a light pink, almost white. |
| Lastingness of flowers. | Longer than the species. | Shorter than 'OOSMANPIN2'. |
| Luster of flower petals. | Matte; dull. | Glossy; shiny. |

COMPARISON WITH THE MOST SIMILAR *MANDEVILLA* CULTIVAR KNOWN TO THE INVENTOR

Plants of the new cultivar 'OOSMANPIN2' may be distinguished from the most similar known commercial comparator, *Mandevilla* 'FISRIX PINKA' (U.S. Plant Pat. No. 20,644), by the characteristics described in Table 2.

TABLE 2

| Characteristic | 'OOSMANPIN2' | 'FISRIX PINKA' |
|---|---|---|
| Branching habit. | Less branching. | More freely branched. |
| Leaf attitude. | Leaves are more erect. | Leaves are more relaxed. |

TABLE 2-continued

| Characteristic | 'OOSMANPIN2' | 'FISRIX PINKA' |
|---|---|---|
| Leaf apex. | Short apiculate. | Acuminate. |
| Flower color when fully opened. | Pink. | Red-purple. |

That which is claimed is:

1. A new and distinct variety of *Mandevilla* plant named 'OOSMANPIN2', substantially as described and illustrated herein.

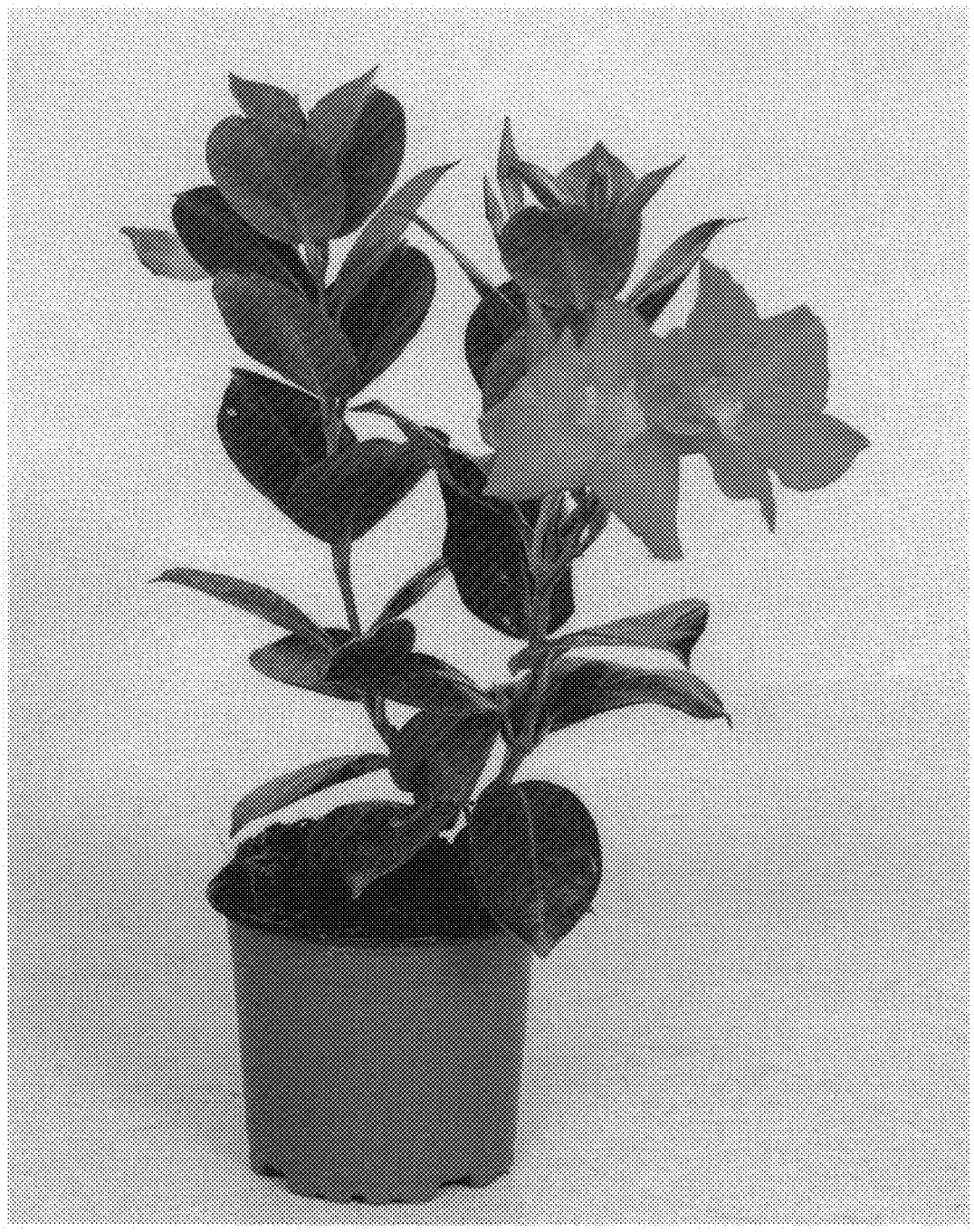

* * * * *